United States Patent
Venturini et al.

(10) Patent No.: US 11,406,434 B2
(45) Date of Patent: Aug. 9, 2022

(54) BONE PLATE

(71) Applicant: ORTHOFIX S.R.L., Bussolengo (IT)

(72) Inventors: Daniele Venturini, Povegliano Veronese (IT); Marco Magni, Ferrara (IT); Andrea Zaccaria, Tregnago (IT)

(73) Assignee: Orthofix S.R.L., Bussolengo (IT)

( * ) Notice: Subject to any disclaimer, the term of this patent is extended or adjusted under 35 U.S.C. 154(b) by 207 days.

(21) Appl. No.: 16/481,293

(22) PCT Filed: Mar. 12, 2018

(86) PCT No.: PCT/EP2018/056022
§ 371 (c)(1),
(2) Date: Jul. 26, 2019

(87) PCT Pub. No.: WO2018/172113
PCT Pub. Date: Sep. 27, 2018

(65) Prior Publication Data
US 2021/0290280 A1    Sep. 23, 2021

(30) Foreign Application Priority Data

Mar. 20, 2017   (IT) .................... IT102017000030628

(51) Int. Cl.
*A61B 17/80* (2006.01)
*A61B 17/70* (2006.01)

(52) U.S. Cl.
CPC ...... *A61B 17/8061* (2013.01); *A61B 17/7059* (2013.01); *A61B 17/8014* (2013.01); *A61B 17/8028* (2013.01)

(58) Field of Classification Search
CPC . A61B 17/8014; A61B 17/8061; A61B 17/80; A61B 17/7059; A61B 17/808;
(Continued)

(56) References Cited

U.S. PATENT DOCUMENTS 4,683,878 A * 8/1987 Carter ................ A61B 17/8014
606/97
4,905,680 A * 3/1990 Tunc ...................... A61B 17/80
606/280

(Continued)

FOREIGN PATENT DOCUMENTS

FR    2405061    5/1979

OTHER PUBLICATIONS

International Searching Authority/European Patent Office, "Notification of Transmittal of the International Search Report and The Written Opinion of the International Searching Authority, or the Declaration," for PCT/ep2018/056022, dated Jun. 6, 2018, 13 pages.

*Primary Examiner* — Marcela I. Shirsat
(74) *Attorney, Agent, or Firm* — Haynes and Boone, LLP (57) ABSTRACT

The present invention relates to an internal fixator device (1) of the bone plate type to be used as synthesis means in anatomical regions or epiphyses/metaphyses with poor coating of soft tissue, of the type comprising a two-lobe or eight-shaped bone plate (2) comprising a pair of lobed portions (23, 24) which are linked by a central linking portion (15) and in each of which at least one through-hole (3, 4) is formed to receive a corresponding bone fixation screw (5). Advantageously, each of the pair of lobed portions (23, 24) of the bone plate (2) has an upper surface (7) inclined relative to a reference plane (X) coinciding with a second upper surface of the linking central portion (15) of the bone plate (2), and a lower surface (6) configured for contact with the bone and inclined relative to the same reference plane (X) with a smaller inclination.

9 Claims, 8 Drawing Sheets

(58) Field of Classification Search
CPC ............ A61B 17/8047; A61B 17/8085; A61B 17/8028; A61B 17/8052; A61B 17/8635; A61B 17/1757; Y10S 606/90
USPC .................................................. 606/291, 286
See application file for complete search history.

(56) References Cited

U.S. PATENT DOCUMENTS

| | | | |
|---|---|---|---|
| 6,565,571 B1* | 5/2003 | Jackowski | A61B 17/1728 606/286 |
| 8,257,406 B2* | 9/2012 | Kay | A61B 17/8061 606/286 |
| 8,273,111 B2 | 9/2012 | Amato et al. | |
| 8,685,069 B2* | 4/2014 | Courtney | A61B 17/8057 606/291 |
| 2004/0111089 A1* | 6/2004 | Stevens | A61B 17/1728 606/86 B |
| 2004/0204712 A1* | 10/2004 | Kolb | A61B 17/1757 606/71 |
| 2006/0106387 A1* | 5/2006 | Fanger | A61B 17/8047 606/281 |
| 2009/0318977 A1* | 12/2009 | Di Giacomo | A61B 17/809 606/286 |
| 2012/0059424 A1 | 3/2012 | Epperly et al. | |
| 2013/0204249 A1* | 8/2013 | Zhao | A61B 17/1764 606/60 |
| 2013/0325073 A1* | 12/2013 | Sikora | A61B 17/808 606/286 |
| 2017/0065312 A1* | 3/2017 | Lauf | A61B 17/8047 |
| 2017/0215931 A1* | 8/2017 | Cremer | A61B 17/80 |
| 2018/0021050 A1* | 1/2018 | Little | A61B 17/8085 606/280 |
| 2019/0133643 A1* | 5/2019 | Magni | A61B 17/80 |
| 2020/0323569 A1* | 10/2020 | Venturini | A61B 17/8635 |

\* cited by examiner

BONE PLATE

CROSS REFERENCE TO RELATED APPLICATIONS

The present application is the U.S. national phase of International Application No. PCT/EP2018/056022, filed Mar. 12, 2018, which designated the U.S. and claims priority to and the benefit of the Italian Application No. 102017000030628, filed Mar. 20, 2017, both of which are hereby incorporated by reference in their entirety as if fully set forth below in its entirety and for all applicable purposes.

FIELD OF THE INVENTION

The present invention relates to an improved internal fixator device of the bone plate type intended to be used as synthesis means in anatomical regions with poor coating of soft tissue, of the type comprising a bone plate in which two through-holes are formed to receive corresponding bone fixation screws.

The invention relates in particular, but not exclusively, to an internal fixator device of the bone plate type which is intended to improve the tolerability for patients of synthesis treatments of fractures or for correction of bone deformations, and which envisages the application of this bone plate underneath the skin, on epiphyses in anatomical regions poorly covered by soft tissues.

The invention has a useful application in particular in the sector of pediatric orthopedics, for example in epiphysiodesis operations performed on ends of deformed long bones of pediatric patients, and the description which follows is provided with non-limiting reference to use in the context of this sector.

In the specific technical sector of the present invention, a number of problems are known to exist, these being due to the low tolerability of bone fixation plates in certain anatomical regions, including the knee, the elbow and the backbone, which do not have relevant thicknesses of soft tissues.

For example, the use of these bone plates on epiphyses situated close to articulations, causes on occasions local inflammations due to the projection of the heads of the bone fixation screws from the plates.

The bone plate is positioned by means of two fixation screws which fasten it respectively to the epiphysis and to the metaphysis, in the convex zone of the bone deformation. Both the metaphyseal and the epiphyseal portions of the bone plate have in fact at least one through-hole designed to receive a corresponding fixation screw.

In this technical sector, particular bone plates shaped in the manner of an "8" are known, these being fastened to the bone by means of fixation screws which are able to diverge, so as to prevent compression of the growth cartilage and delicately assist the natural growth process of the physis and of the bones, without the need for a more invasive osteotomy intervention.

The fixation screws are fastened loosely inside the respective through-holes of the bone plate so as to be able to vary their angle of inclination, adapting gradually to the bone growth process. In fact, during the growth of the physeal tissue, the fixation screws are subject to a pulling action which gradually causes angular diverging thereof, namely the two screws become inclined away from each other relative to a center plane passing through the physis.

PRIOR ART

A solution currently adopted by the prior art is described in the US patent application U.S. Pat. No. 8,273,111 which relates to a fixator device of the bone plate type for controlling bone growth, in particular for correcting bone deformations. This device may comprise a bone plate having a stepped profile defined by a first level, a second level and an intermediate ramp connecting them, each level being provided with a threaded hole for receiving a bone fixation screw. FIG. 3 of U.S. Pat. No. 8,273,111 also shows a variant of this bone plate, having an intermediate portion in the form of an arch or a hump, which is used depending on the anatomical shape of the specific patient or depending on the bone. In this way it, U.S. Pat. No. 8,273,111 proposes to avoid overloading the physis of the bone and damaging it during the correction, for example when the bone plate must be implanted in a patient of pediatric age in order to correct a non-symmetrical growth or an anatomical deformation.

Furthermore, in order to improve the tolerability of these bone plates in anatomical regions where there is poor coating of soft tissues, a prior art solution which could be referred to as "integrated washer" is known, which locally increases the thickness of the bone plate towards the bone in the region of the through-holes for receiving the fixation screws. In this way it is possible to reduce partially the projection of the screw heads from the upper profile of the plate, but only during implantation.

Although advantageous from many points of view and substantially fulfilling its purpose, the plate above described in this prior art has a number of drawbacks as well, for example the very same integrated washer in the plate, in the lower surface thereof, limits the area of contact with the bone.

Furthermore, the plate configurations used in the prior art to avoid crushing of the growth cartilage may on some occasions affect the strength of the bone plate itself and make it relatively fragile.

The technical problem underlying the present invention is that of devising an improved synthesis means, comprising an internal fixator device of the bone plate type with an improved structure for improving tolerability when applied in anatomical regions poorly coated by soft tissues. The bone plate according to the invention envisages structural and functional characteristics such as to prevent lateral crushing of the growth cartilage and favor removal of said bone plate when its presence is no longer required.

Another object of the invention is to provide a fixator device with a simple and low-cost structure, which also ensures a certain strength for the whole duration of its implantation period.

A further object of the invention is to ensure the tolerability for patients of any degree of projection of the heads of the bone fixation screws, also when the corresponding bone plate is situated on epiphyses coated only by thins layers of muscle or soft tissues.

SUMMARY OF THE INVENTION

A proposed solution of the present invention is to provide a bone plate with two opposite lobed portions having a rounded profile and having respective upper and lower surfaces which are slightly inclined relative to a reference plane of their linking central portion, so as to taper towards the respective ends.

Based on this proposed solution the technical problem is solved by an internal fixator device of the bone plate type to be used as synthesis means in anatomical regions or epiphyses with poor coating of soft tissue, of the type comprising a two-lobe or eight-shaped bone plate comprising a pair of lobed portions which are linked by a central linking portion, wherein in each of said pair of lobed portions at least one through-hole is formed to receive a corresponding bone fixation screw, wherein each of said pair of lobed portions of the bone plate has an upper surface inclined relative to a reference plane coinciding with a second upper surface of said linking central portion of the bone plate, and a lower surface configured for contact with the bone and inclined relative to the same reference plane with a smaller inclination.

More particularly, said upper surface is inclined at a first predetermined angle relative to the same reference plane, whereas the lower surface is inclined at a second predetermined angle, the inclination of the second angle of the lower surface being smaller than the inclination of the first angle of the upper surface.

It should be noted that said inclination angle of the upper surface is variable within a range of values from 6° to 15°. Preferably, however, said inclination angle of the upper surface is equal to 12°.

Conversely, the inclination angle of the lower surface is preferably fixed and equal to 5°.

The opposite ends of the bone plate gradually taper in directions away from the center of the said bone plate as a result of the different inclinations of the surfaces of the lobed portions.

The lower surface at the opposite ends of the bone plate, returns in a flat configuration which is not inclined relative to said reference plane, so as to allow insertion of an instrument for removing the bone plate.

The bone plate according to the present invention has two lobes and is substantially eight-shaped.

It is also envisaged providing a recess or cavity transverse to a longitudinal axis of the bone plate and formed only on the lower surface in the region of said linking central portion.

The bone plate according to the present invention also has a slightly arched cross-sectional profile of the opposite lower surface and upper surface.

More particularly, the radii of curvature of the arched profile of these opposite surfaces are slightly different from each other.

More specifically, the radius of curvature of the lower surface is greater than the radius of curvature of the upper surface, in order to improve the adhesion with the bone.

The features and advantages of the internal fixator device of the bone plate type according to the present invention, will emerge from the description hereinbelow of a preferred embodiment provided by way of a non-limiting example with reference to the accompanying drawings.

DETAILED DESCRIPTION OF PREFERRED EMBODIMENTS

Figure 1:
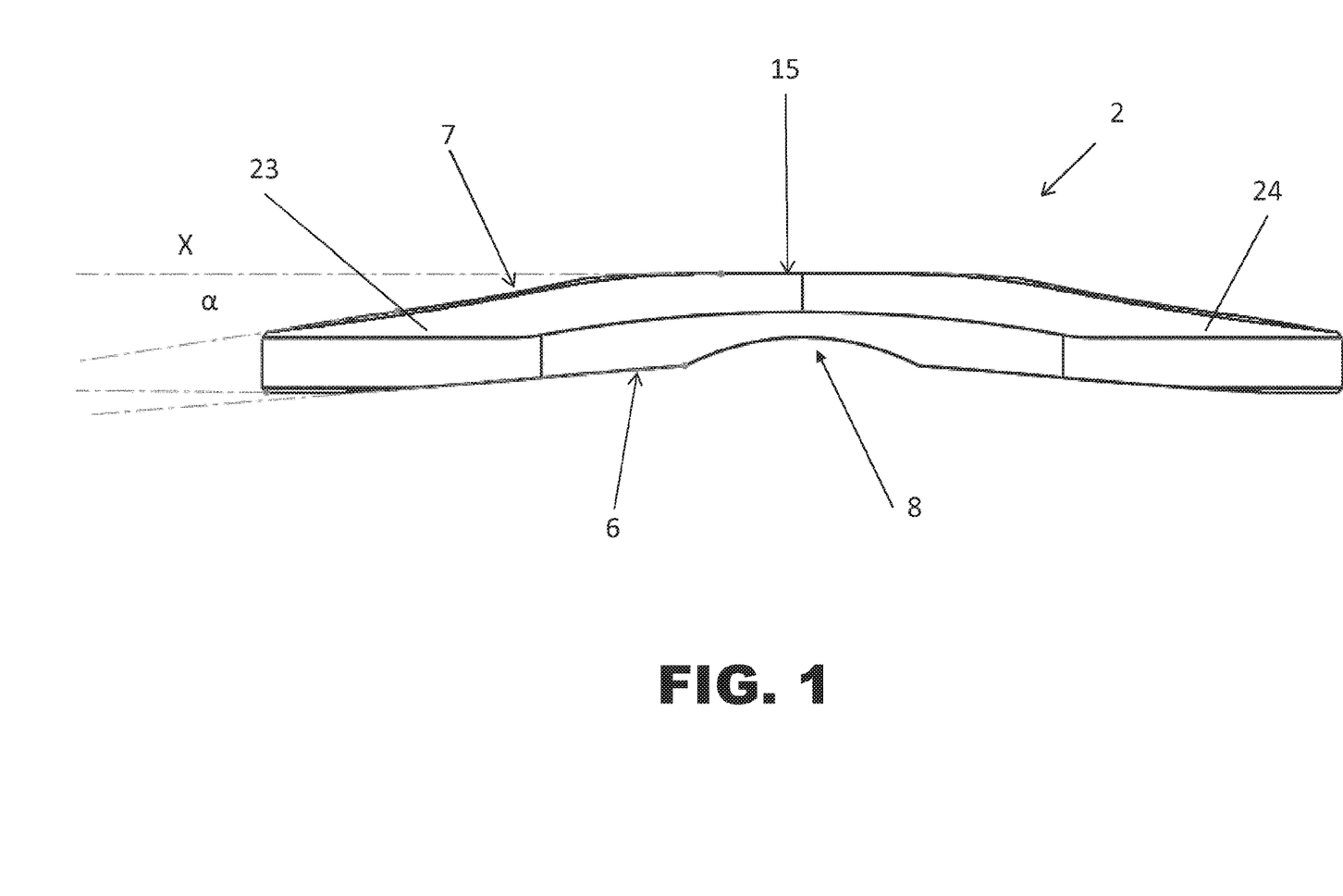
FIG. 1 shows a side view of an internal fixator device of the bone plate type provided in accordance with the present invention.

With reference to these figures and in particular to the example of FIG. 1, 1 denotes overall and in schematic form an internal fixator device comprising a bone plate 2 for improving the tolerability of this bone plate in anatomical regions where there is poor or limited coating of soft tissues.

The fixator device 1 according to the present invention is particularly suitable, albeit not exclusively, for use in orthopedics applications in order to resolve bone fractures of bone fragments or correct deformations of long bones in pediatric and/or adolescent patients with application of the fixator device straddling the physis of these bones.

This bone plate 2 is preferably made of a rigid biocompatible material (for example titanium) and has a two-lobe and/or eight-shaped form, having a greater extension in a longitudinal direction than in a transverse direction.

The bone plate 2 does not have a uniform thickness and has two opposite surfaces, 6 and 7, wherein surface 6 is provided so as to be arranged in contact with a bone surface. For simpler illustration, in the following of this description, said first surface will be indicated as lower surface 6 and the second surface, situated opposite it, will be indicated as upper surface 7 of the bone plate 2.

Advantageously, a recess 8 or cavity is provided transverse to the longitudinal axis of the bone plate 2 and is formed only on the lower surface 6.

Any positional references used in the present description and comprising terms such as "lower" or "upper", "below" or "above", or similar terms, will always be in relation to the orientation of the aforementioned surfaces 6 and 7.

The two-lobe eight-shaped bone plate 2 comprises a first portion 23 and a second portion 24 which are designed to be associated with, respectively, the epiphysis and metaphysis of a long bone of a pediatric patient, for example a bone having an angular deformation to be corrected with application of the internal fixator device 1 according to the present invention.

Figure 3:
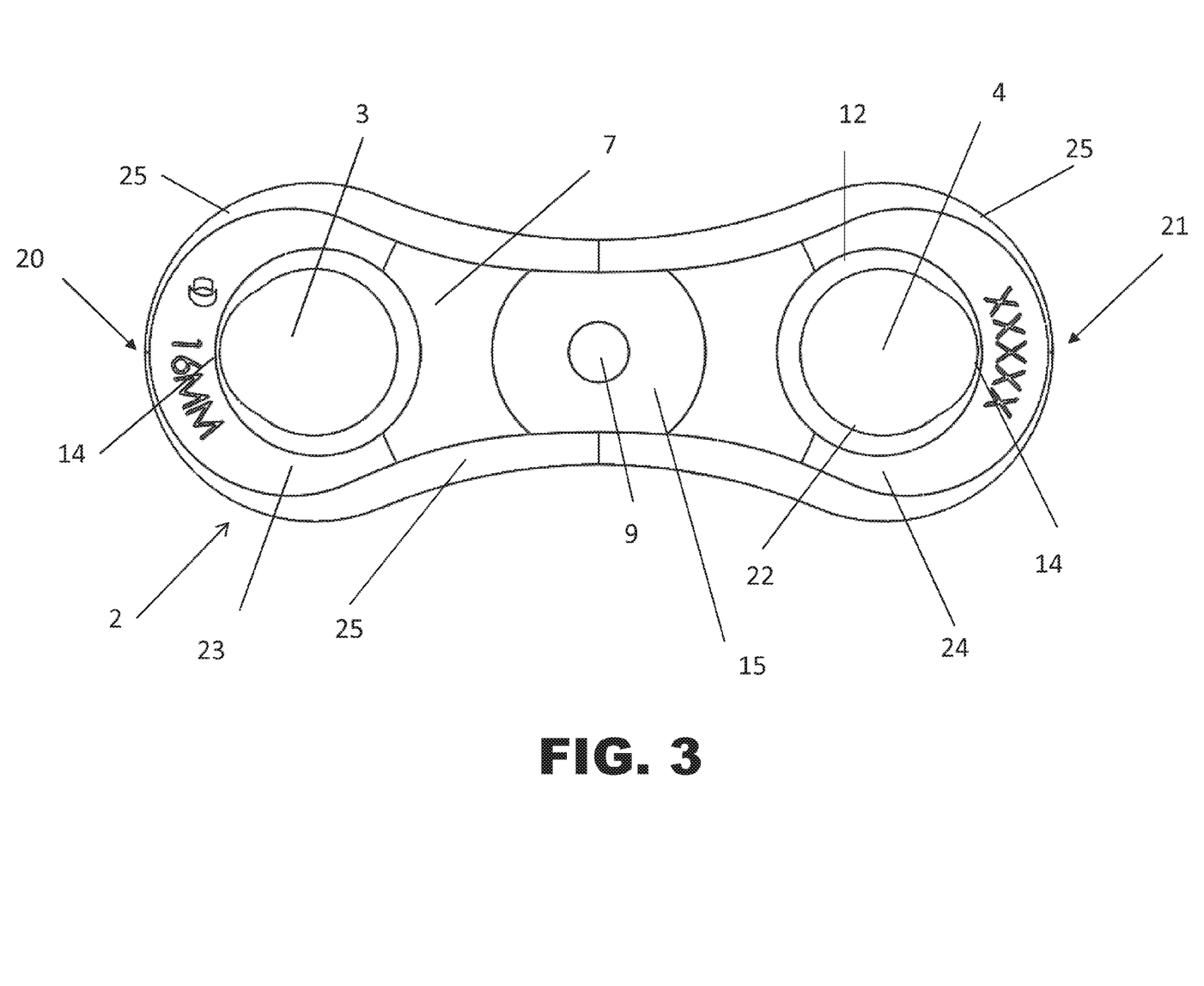
FIG. 3 shows a top view of the bone plate shown in FIG. 1.

As especially visible in FIG. 3, The two portions of the "8" shape are interconnected by means of a linking central portion 15, where there is a sole localized narrowing of the bone plate 2.

The aforementioned recess 8 in the lower surface 6 is provided in this linking central portion 15 of the bone plate 2. This recess 8 has an arched shape relative to the transverse axis of the bone plate 2 and is provided to allow growth of the physis when the bone plate is implanted.

The central linking portion 15 has a guiding through-hole 9 designed to facilitate the initial implantation of the bone plate 2 by means of a guide wire (not shown) so that the central linking portion 15 is located astride the physis growing between the epiphysis and the metaphysis.

The bone plate 2 has an essentially symmetrical shape with respect to a transverse plane passing through the center of the linking portion 15.

The zones of the first portion 23 and of the second portion 24 located at the maximum distance from the transverse plane passing through the center of the central linking portion 15, define respectively a first end 20 and a second end 21 of the bone plate 2.

The first portion 23 has, passing through it, a first through-hole 3 designed to receive a fixation screw 5 (not shown).

The second portion 24 also has, passing through it, a second through-hole 4 designed to receive a corresponding fixation screw 5 (not shown).

The bone plate 2 has perimetral edges 25 which are smoothed and rounded along both the lower surface 6 and the upper surface 7.

Figure 4:
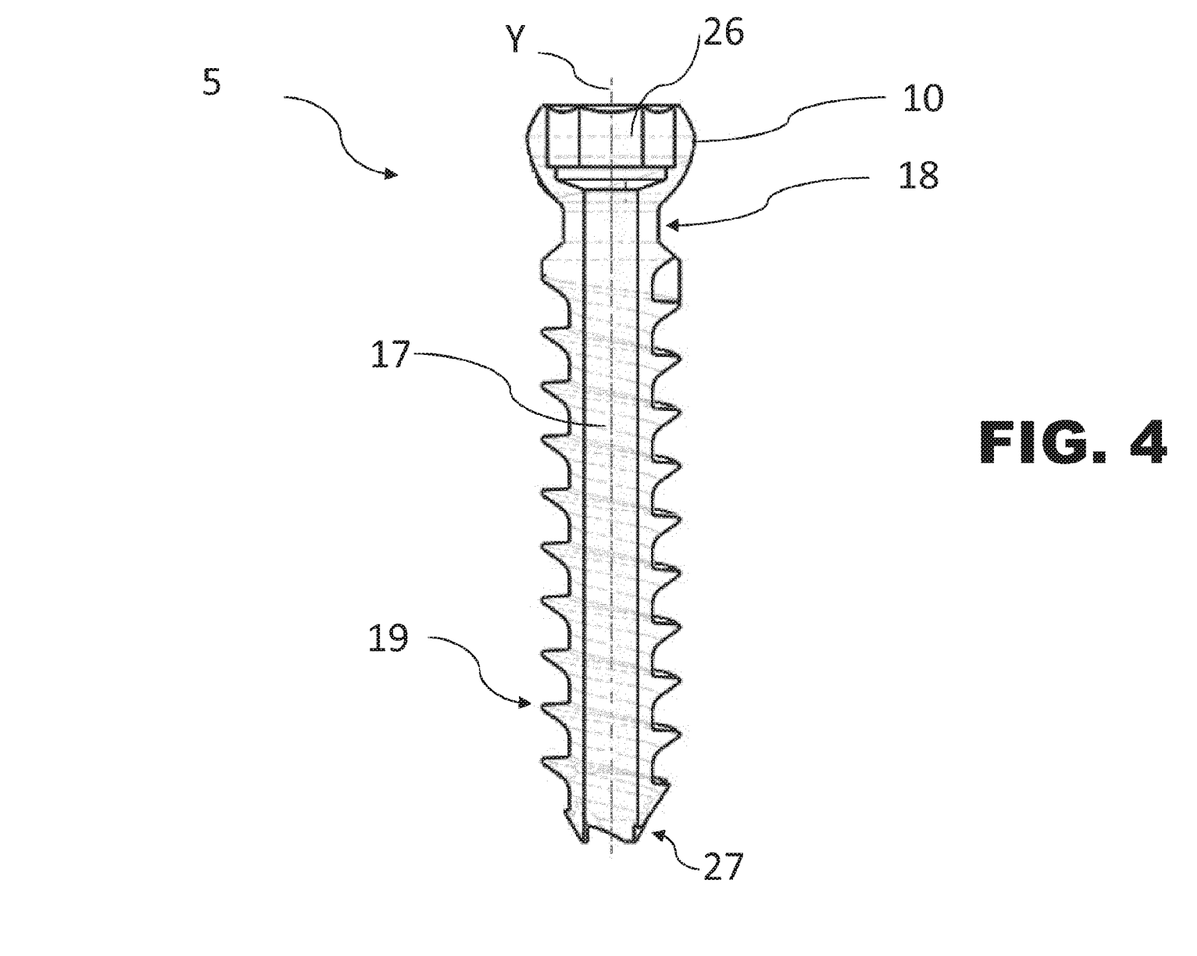
FIG. 4 shows a cross-section side view of a fixation screw used with the fixator device according to FIG. 1.

In a preferred embodiment, each fixation screw 5, which can be seen in its entirety in FIG. 4, comprises a preferably spheroidal head 10 located at the end of the stem directed along a longitudinal axis Y. The stem has a non-threaded portion 18 adjacent to the head 10, a following threaded portion 19, preferably with a triangular shaped thread, and finally a self-tapping tip 27 situated opposite the head 10. The stem is passed through by an internal guide pipe 17 which opens out inside a hexagonal cavity 26 inside the head 10.

Owing to the aforementioned symmetry of the bone plate 2, the through-hole 3 of the first portion 23 and the through-hole 4 of the second portion 24 are equal and opposite to each other. For simpler description, the internal form of only hole 4 is described below, this description being applicable symmetrically to both of the holes 3, 4.

Figure 2:
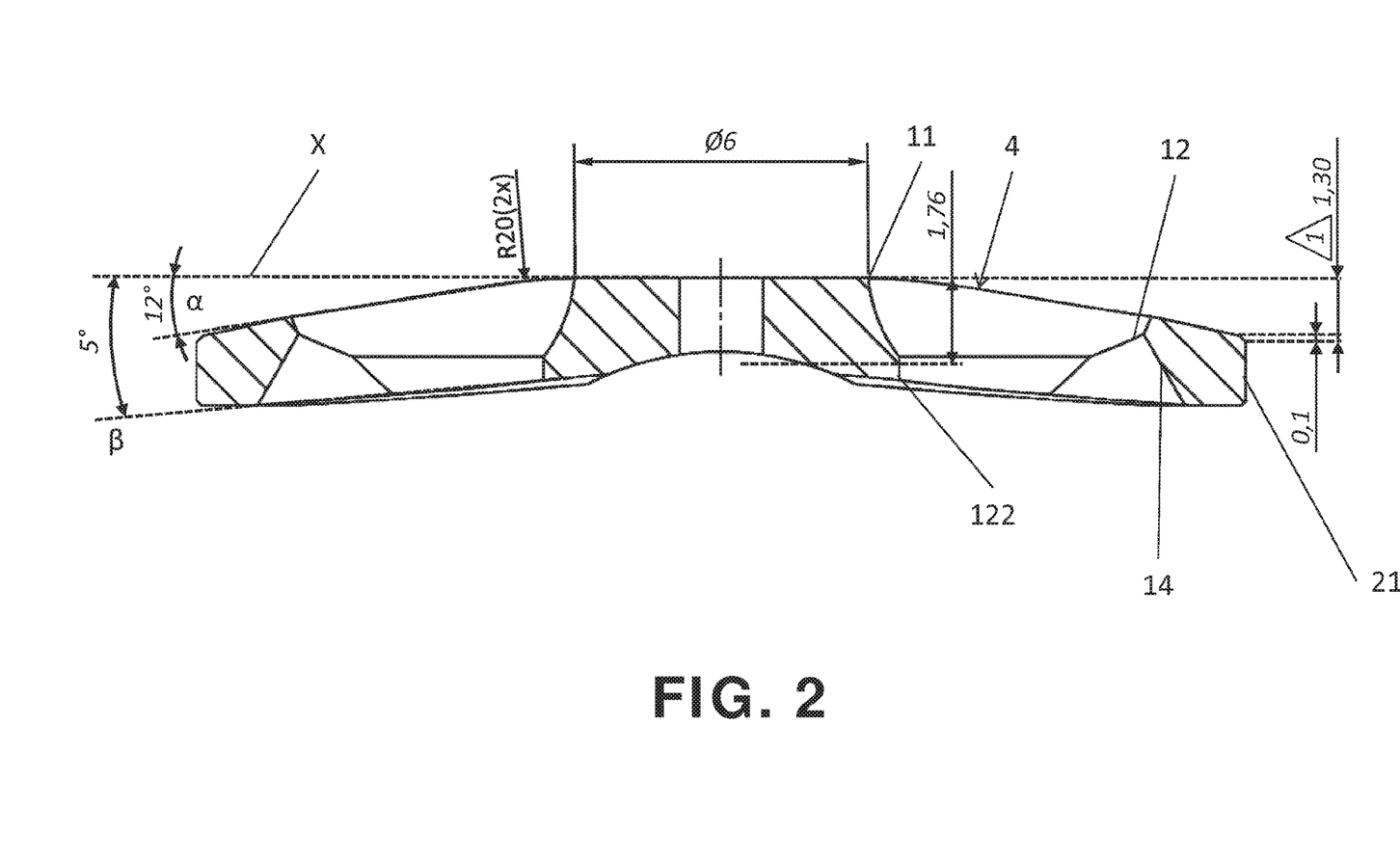
FIG. 2 shows a cross-section side view of the internal fixator device of the bone plate type according to FIG. 1.

The hole 4 comprises a cup-shaped—preferably semi-spherical—seat 12 for pivotably seating the head 10 of the fixation screw 5.

A cylindrical bore 22, which opens out in the bottom of said cup-shaped seat 12, is intended to receive the stem 18 of said fixation screw 5.

At least one recessed zone 14 leading into the cup-shaped seat 12 and into the cylindrical bore 22, is provided on a bottom portion of the cup-shaped seat 12 towards the end 21 of the bone plate 2 on the side of the lower surface 6.

The cup-shaped seat 12 defines a spherical zone for engagement with the head 10 seated inside it, allowing complete freedom of movement of the stem 18 of the screw 5. In particular, the fixation screw 5 may thus be inclined in a longitudinal plane relative to the bone plate 2, in a direction away from the center plane passing through the physis, until an end-of-travel or stop point is reached.

The cup-shaped seat 12 comprises in particular an entry section 11—preferably circular—designed to allow the introduction of the head 10 of the fixation screw 5 inside the hole 4 and an exit section 122, having a size at least locally smaller than the entry section 11 for allowing retention of the head 10 of the fixation screw 5 inside the cup-shaped seat 12.

As already mentioned, the cup-shaped seat 12 has a preferably semi-spherical shape, with its axis perpendicular to the bone plate 2 and passing substantially through the center of the entry section 11.

The cylindrical bore 22 extends coaxially with the cup-shaped seat 12 and has a diameter which is the same as that of the exit section 122.

The recessed zone 14 leads into the cup-shaped seat 12, resulting in a widening, at the bottom, of the exit section 122 in a direction away from the linking central portion 15.

The recessed zone 14 may be formed for example by means of an inclined, cylindrical or conical hole leading inside the cup-shaped seat 12. This recessed zone 14 in the form of a cylindrical or conical hole may have a main diameter with dimensions greater than, or at least equal to, the diameter of the non-threaded upper portion 18 of the stem of the fixation screw 5 and having an axis inclined at a predetermined angle with respect to the axis of the through-hole 4.

The recessed zone 14 opens out on the outer lateral periphery of the cup-shaped seat 12 and extends downwards and outwards, namely towards the respective end 20 or 21, until it emerges on the lower surface 6 of the bone plate. The recessed zone 14 remains in communication with the cylindrical bore 22 along its entire extension.

Advantageously, according to the invention, the bone plate 2 has a particular shape of its opposite surfaces 6 and 7 compared to the solutions of the prior art.

More particularly, the bone plate 2 is flat only in the top part of the linking central portion 15, which links together the two lobed portions 23 and 24.

Taking as a reference the plane X in which this linking central portion 15 lies, the opposite upper surfaces of the two lobed portions are inclined at a predetermined angle α.

Preferably, this angle α is chosen so as to be equal to twelve degrees (12°).

However, it is important to note that this angle α may change with an increase in the geometrical dimensions of the bone plate 2. In fact, it is convenient to provide plates of substantially increasing dimensions, depending on the application needs, although with a proportional increase in all the sections thereof, or in any case homothetic, wherein the angle α may vary within a range of values of between six and fifteen degrees (6° and 15°).

Figure 8:
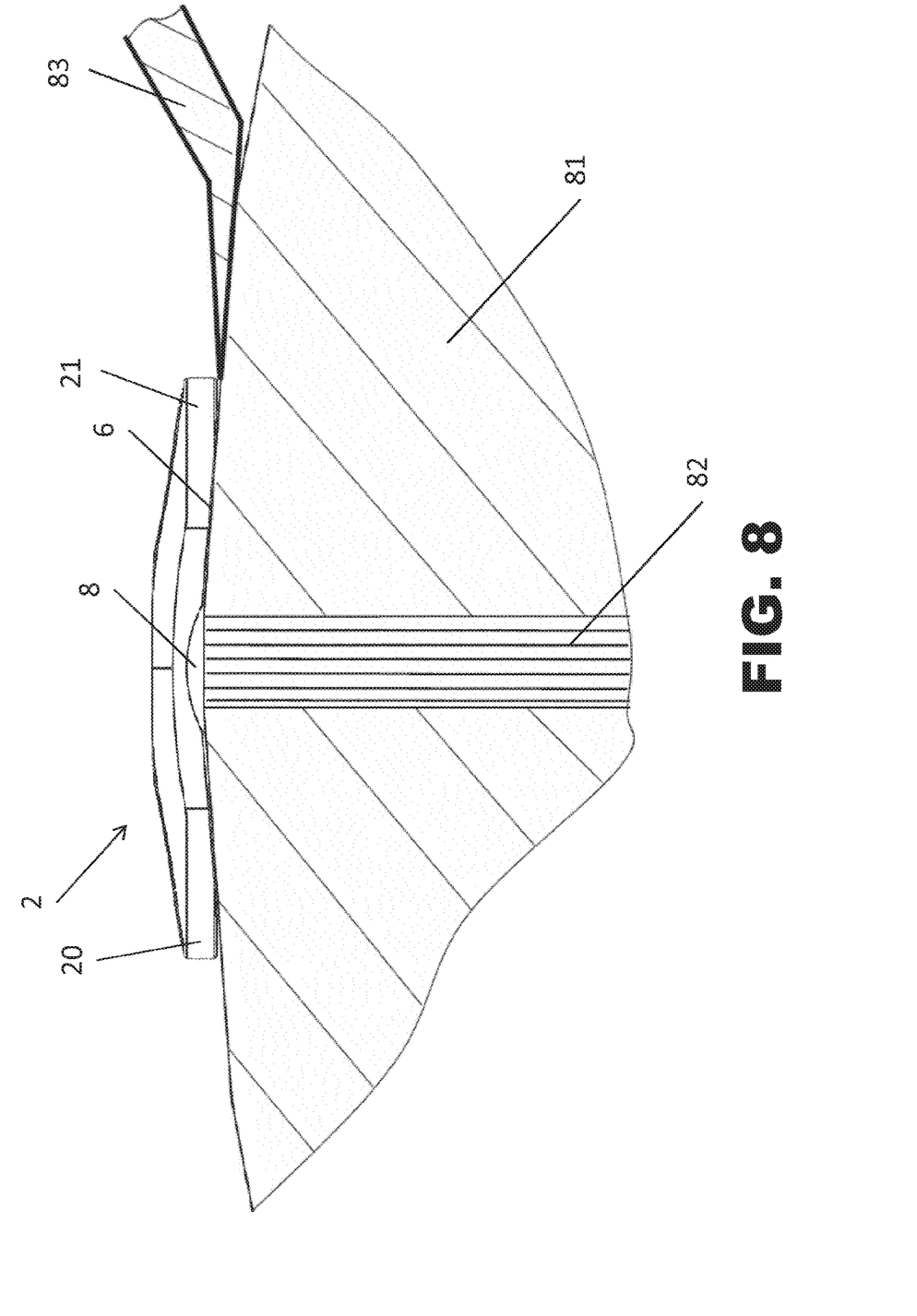
FIG. 8 shows a schematic view of a further example of application of the bone plate according to the invention.

Also, the lower surfaces of the two opposite lobed portions 23 and 24 are inclined with respect to the same upper reference plane X. The lower surfaces are intended to adhere to the bone, as shown in FIG. 8.

These lower surfaces are, however, inclined at a smaller angle β. Preferably, this angle β is chosen so as to be equal to five degrees (5°).

Even with an increase in the dimensions of the bone plates, the inclination angle β of the lower surfaces 6 preferably remains constant.

In other words, each of the two lobed portions 23 and 24 of the bone plate 2 has an upper surface 7 inclined relative to a reference plane X coinciding with the surface of the linking central portion 15 of the bone plate 2, and a lower surface 6 in turn inclined relative to same reference plane X, but with a smaller inclination.

Namely, if the upper surface 7 is inclined at a predetermined angle α and the lower surface 6 is inclined at a predetermined angle β, the inclination angle β of the lower surface is smaller than the inclination angle α of the upper surface 7.

As a result of these different inclinations of the upper and lower surfaces of the lobed portions of the bone plate 2, the opposite ends 20, 21 of the bone plate gradually taper in the direction away from the center 9.

It should be noted that the inclination of the lower surface 6, on both the portions 23 and 24, continues almost up to the ends 20 and 21, but is interrupted at a predetermined distance from the edge, and then becomes flat again and parallel to the plane X in which the linking central portion 15 lies.

It should be furthermore noted that the contact between the bone plate 2 and the bone 81 across the physis 82, takes place on the lower surfaces 6 adjacent to the bottom central recess 8. FIG. 8 shows very clearly the effect of this shape, which interrupts substantially the adhesion of the bone plate 2 at the two opposite ends 20, 21, also as a result of the surface 6 returning into a flat configuration, this allowing access, on at least one side or at one end, for an instrument 83 in order to remove the bone plate.

Advantageously, moreover, the bone plate 2 according to the present invention also has a slightly arched cross-sectional profile of the opposite lower surface 6 and upper surface 7.

Figure 6:
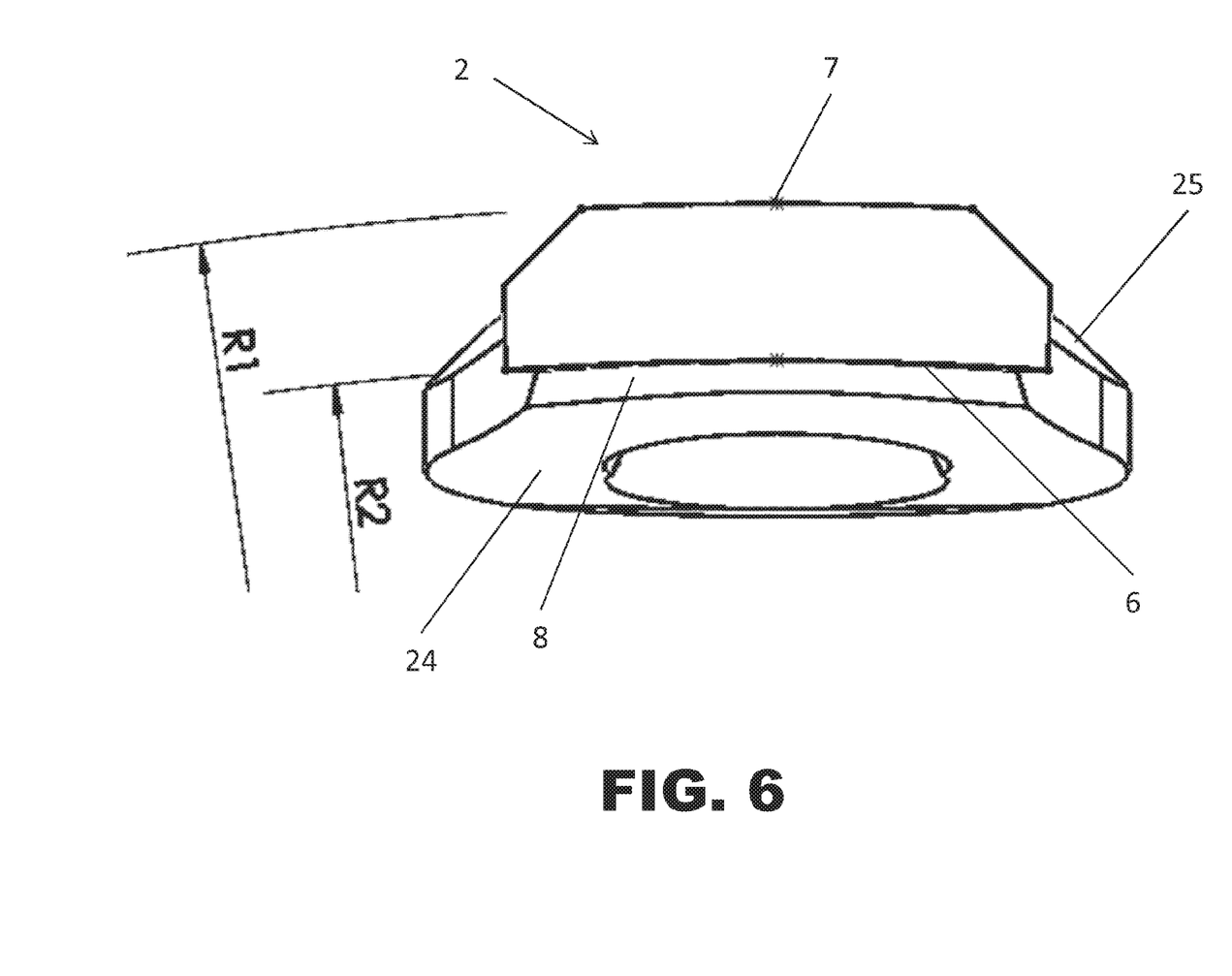
FIG. 6 shows a cross-section view of the bone plate according to FIG. 1.

As clearly shown in the cross-section of FIG. 6, the radii of curvature of the arched profile of these surfaces 6 and 7, are slightly different from each other.

The radius of curvature R2 of the lower surface 6 is greater than the radius of curvature R1 of the upper surface 7.

This arched shape in the direction perpendicular to the main longitudinal axis of the bone plate 2 allows a better adhesion or fit onto the bone, which normally has a curved profile, than a bone plate which is perfectly flat. Consequently, a better stability is obtained.

Figure 7:
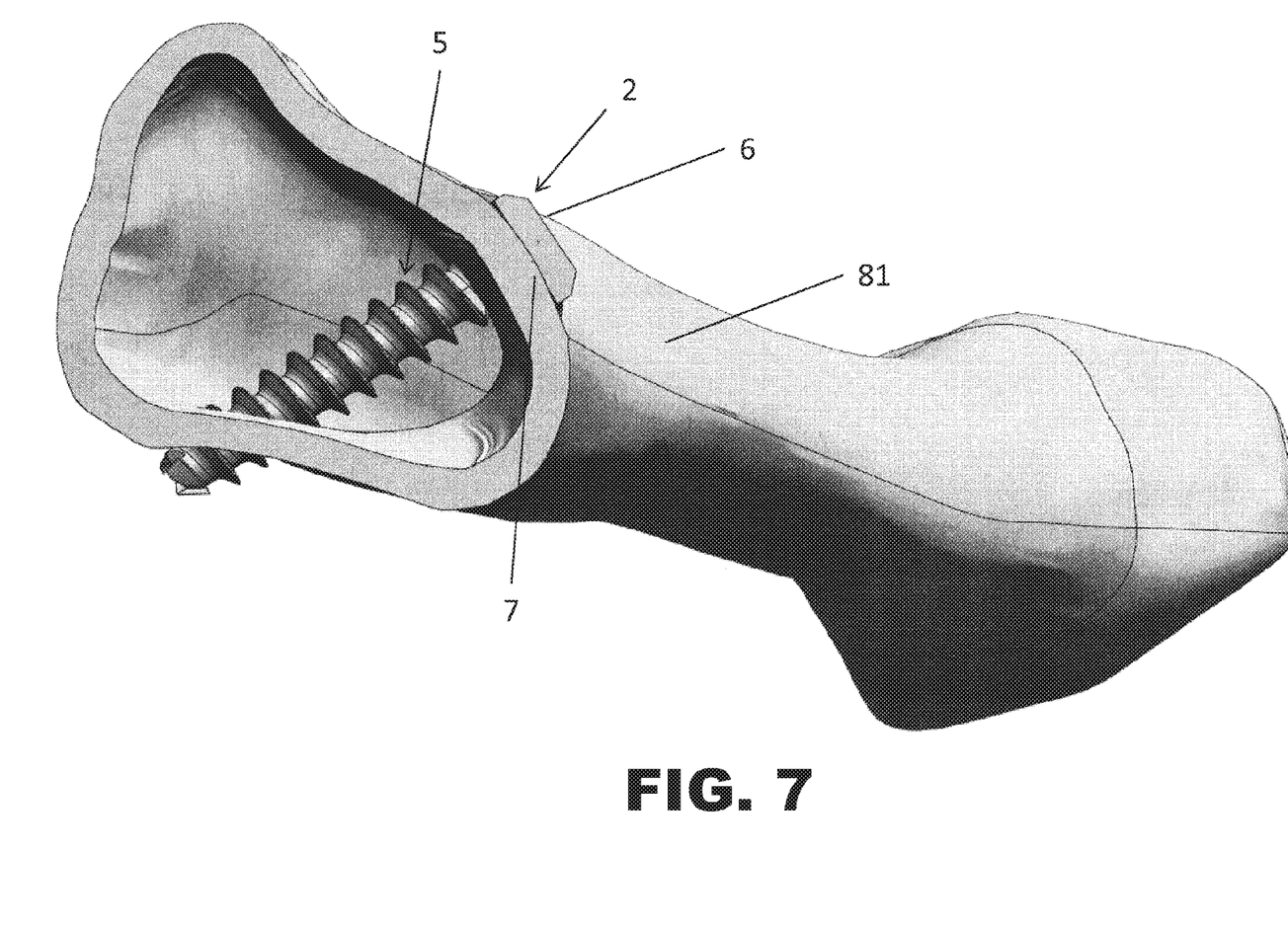
FIG. 7 shows a partial cross-section perspective view of an example of application of the internal fixator device of the bone plate type according to the present invention.

In FIG. 7 it is possible to see an example of application of the bone plate 2, showing a cross-section of the bone plate 2 in contact with the bone 81 with a fixation screw 5 fully inserted inside the bone.

From this FIG. 7 it is also possible to appreciate a further advantage associated with the lower profile of the bone plate 2, which allows easier positioning of the longitudinal axis of the bone plate 2 relative to the bone 81.

For completeness of description, it is pointed out that the maximum thickness "s" of the bone plate 2 is preferably one eighth smaller than its maximum longitudinal extension "L", from the end 20 to the end 21. The maximum thickness "s" relates to the thickness of the point on the bone plate 2 where there is a change in inclination of the upper surface 7 of the two portions 23 and 24 with respect to the linking central portion 15.

The maximum thickness "s" may be chosen in a range of between one eighth and one twelfth of the maximum longitudinal extension "L".

In a preferred embodiment, this maximum thickness "s" may be chosen in a range of between 1.5 and 2.3 mm, with a machining tolerance of at least 5%.

More particularly, the maximum thickness "s" is chosen as being equal to 2.1 mm.

Moreover, the thickness "s" of the bone plate 2 in the region of the cavity 8 is variable within a range of between 1.3 and 1.7 mm, in this case too with a machining tolerance of at least 5%.

In a preferred embodiment this thickness "s" is chosen as being equal to 1.5 mm when the thickness of the bone plate 2 is equal to 2.1 mm.

A use of the bone plate fixator device 1 according to the present invention is now described.

Once a relatively uninvasive incision has been made in the patient's skin and flesh, the bone plate 2 may be positioned astride the physis 82 so that the two lobed portions 23 and 24 are located respectively in contact with the epiphysis and the metaphysis of the bone 81 to be treated.

Advantageously, the inclined end 20 or 21 facilitates insertion and sliding underneath the tissues, this allowing an incision of smaller length to be made, with less discomfort for a patient, in particular a patient of pediatric age.

A fixing wire inserted in the cartilage of the physis through the through-hole 9 in the linking central portion 15 of the bone plate 2, allows the bone plate 2 to be fixed in position, albeit provisionally.

The fixation screws 5 are initially inserted inside the holes 3, 4 so as to penetrate into the corresponding epiphyseal and metaphyseal portions of the bone 81 until the head 10 reaches and comes into contact with the cup-shaped seat 12 and the axis of the cup-shaped section 12 coincides with the axis of the fixation screw 5.

Figure 5:
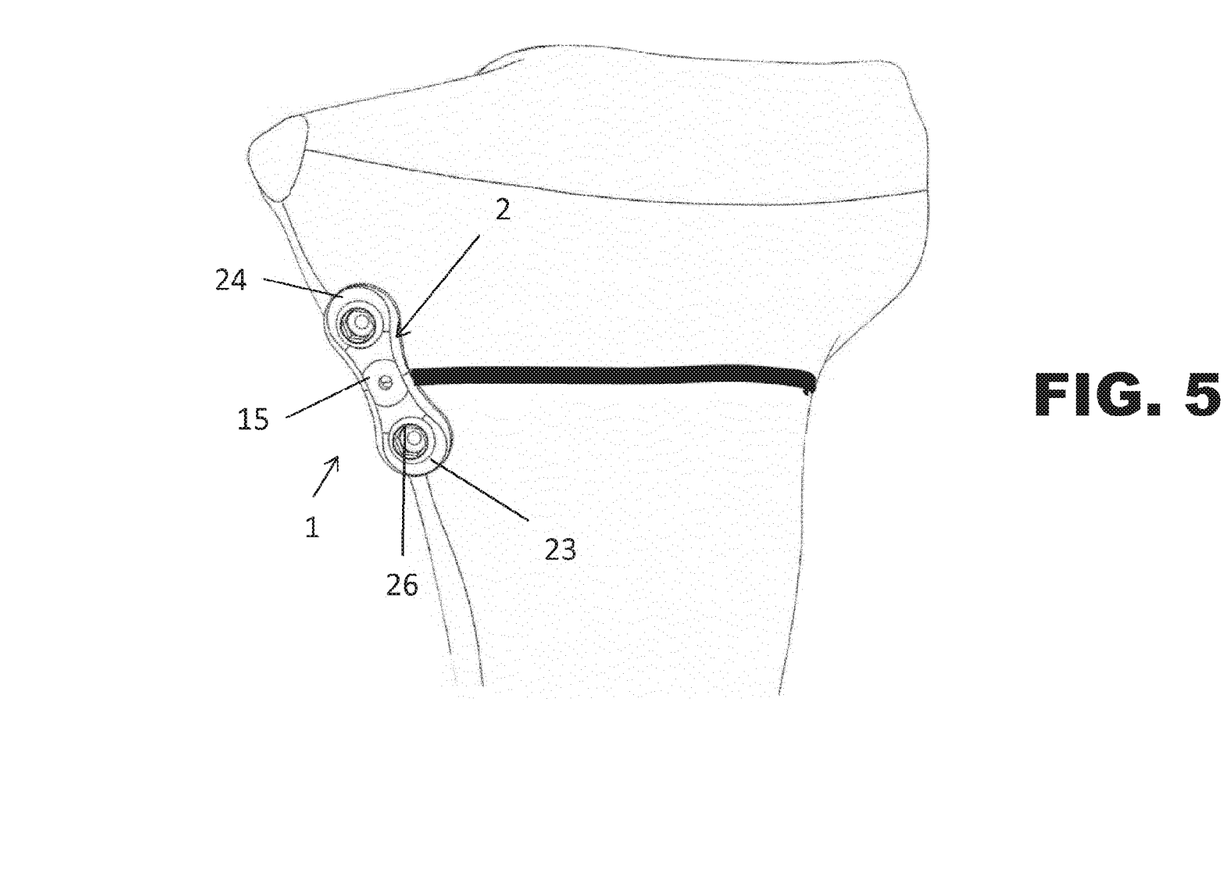
FIG. 5 shows a schematic perspective view of an application of the internal fixator device according to the invention.

The suitable thickness "s" of the bone plate 2 allows the head of the screws 5 to be seated initially almost concealingly inside the respective receiving seats 12, as shown in FIG. 5.

During the growth of the physeal tissue the fixation screws 5 are subject to a pulling action which causes angular diverging thereof during the course of the whole treatment, namely a rotation of the fixation screws 5 in a longitudinal plane relative to the bone plate 2 and in a direction away from the central linking portion 15.

The presence of the recessed zone 14 ensures the provision of an end-of-travel contact between the stem of the fixation screws 5 and the bottom edges of the holes 3, 4, in a direction away from the central linking portion 15, namely at the end 20 or 21 respectively.

In this way, it is possible to achieve and ensure that there is angular diverging of the fixation screws 5 which is greater than that which could be obtained if there were no recessed zone 14, allowing the whole assembly of the fixator device 1, i.e. bone plate 2 and fixation screws 5, to follow the bone growth for the entire duration of the treatment.

The greater thickness "s" of the bone plate in the vicinity of the linking central portion 15, than at the ends 20 or 21 of the bone plate, allows the head 10 of the fixation screws 5 to be seated more easily in a concealed manner, also when the screws have been subjected to their maximum angular deviation due to the growth of the physeal tissue.

Advantageously, the bone plate 2 described above has a shape with a rounded profile and no projections, so as to avoid points where friction may occur with the soft tissue surrounding the implant location.

Again advantageously, the aforementioned shape of the bone plate 2 does not require complex and costly manufacturing methods and may be performed entirely by means of machining.

The bone plate according to the invention solves the technical problem and achieves numerous advantages, including also that of preventing breakage of the fixation screws, and ensuring complete correction of the bone deformation by means of a single surgical operation.

The invention claimed is:

1. Internal fixator device of the bone plate type, said internal fixator device being configured to be used in epiphysiodesis operations performed on ends of a deformed long bone of a pediatric patient, said internal fixator device comprising an eight-shaped bone plate with a pair of lobed portions which are linked by a central linking portion,
   wherein in each of said pair of lobed portions one respective through-hole is formed to receive a corresponding bone fixation screw which is configured to fasten each of said pair of lobed portions respectively to an epiphysis or to a metaphysis of the long bone,
   wherein each of said pair of lobed portions of the bone plate has an upper surface inclined at a first predetermined angle relative to a reference plane coinciding with a second upper surface of said central linking portion of the bone plate, and a lower surface configured for contact with a bone and inclined at a second predetermined angle relative to the same reference plane with a smaller inclination,
   the second angle of the lower surface being greater than 0° and smaller than the first angle of the upper surface.

2. Internal fixator device according to claim 1, wherein said inclination of the first angle of the upper surface ranges from 6° to 15°.

3. Internal fixator device according to claim 2, wherein said inclination of the first angle of the upper surface is equal to 12°.

4. Internal fixator device according to claim 1, wherein said inclination of the second angle of the lower surface is equal to 5°.

5. Internal fixator device according to claim 1, wherein opposite ends of the bone plate gradually taper in directions away from a center of the bone plate.

6. Internal fixator device according to claim 5, wherein said lower surface at said opposite ends returns in a flat configuration not inclined relative to said reference plane.

7. Internal fixator device according to claim 1, comprising a recess or cavity transverse to a longitudinal axis of the bone plate and formed only on the lower surface, in a region of said central linking portion.

8. Internal fixator device according to claim 1, wherein the bone plate has slightly arched cross-sectional profiles of the opposites lower surface and upper surface along the width of the bone plate.

9. Internal fixator device according to claim 8, wherein a radius of curvature of the lower surface is greater than a radius of curvature of the upper surface, in order to improve adhesion with a bone.

\* \* \* \* \*

UNITED STATES PATENT AND TRADEMARK OFFICE
CERTIFICATE OF CORRECTION

PATENT NO. : 11,406,434 B2
APPLICATION NO. : 16/481293
DATED : August 9, 2022
INVENTOR(S) : Daniele Venturini, Marco Magni and Andrea Zaccaria It is certified that error appears in the above-identified patent and that said Letters Patent is hereby corrected as shown below:

In the Claims

Column 9, Line 25, add -- along the width of the bone plate -- after "curvature"

Column 9, Line 26, add -- along the width of the bone plate -- after "curvature"

Signed and Sealed this
Twentieth Day of December, 2022

Katherine Kelly Vidal
*Director of the United States Patent and Trademark Office*